United States Patent
Miyazaki et al.

(10) Patent No.: US 6,911,131 B2
(45) Date of Patent: Jun. 28, 2005

(54) BIOSENSOR

(75) Inventors: Shoji Miyazaki, Ehime (JP); Hiroyuki Tokunaga, Ehime (JP); Masaki Fujiwara, Ehime (JP); Takahiro Nakaminami, Kyoto (JP); Junko Nakayama, Ehime (JP); Eriko Yamanishi, Ehime (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 336 days.

(21) Appl. No.: 09/979,842

(22) PCT Filed: Mar. 28, 2001

(86) PCT No.: PCT/JP01/02558

§ 371 (c)(1),
(2), (4) Date: May 1, 2002

(87) PCT Pub. No.: WO01/73419

PCT Pub. Date: Oct. 4, 2001

(65) Prior Publication Data

US 2002/0179442 A1 Dec. 5, 2002

(30) Foreign Application Priority Data

Mar. 29, 2000 (JP) ............................................. 12-90362
Nov. 9, 2000 (JP) .......................................... 12-342537

(51) Int. Cl.⁷ ....................... G01N 27/327; G01N 21/00
(52) U.S. Cl. ................................... 204/403.14; 422/57
(58) Field of Search ..................... 204/403.01–403.14; 422/57, 68.1

(56) References Cited

U.S. PATENT DOCUMENTS

| | | | |
|---|---|---|---|
| 5,242,793 A | * | 9/1993 | Kariyone et al. ...... 204/403.11 |
| 5,397,451 A | | 3/1995 | Senda et al. ............. 204/403.1 |
| 5,413,690 A | | 5/1995 | Kost et al. ................ 205/777.5 |
| 5,747,669 A | | 5/1998 | Suzuki ....................... 73/23.21 |
| 6,059,946 A | | 5/2000 | Yukawa et al. ......... 204/403.14 |

FOREIGN PATENT DOCUMENTS

| | | |
|---|---|---|
| EP | 0608872 B1 | 8/1994 |
| EP | 0872728 A1 | 10/1998 |
| JP | 2-102448 | 4/1990 |
| JP | 5-87767 | 4/1993 |
| JP | 8-50112 | 2/1996 |
| JP | 9-89831 | 4/1997 |
| JP | 10-78407 | 3/1998 |
| JP | 2000-9679 | 1/2000 |
| JP | 2000-65778 | 3/2000 |
| JP | 2000-81408 | 3/2000 |
| JP | 2001-59846 | 6/2001 |
| WO | 95/03543 | 2/1995 |

OTHER PUBLICATIONS

"Sugar Alcohol" entry downloaded from http://en.wikipedia.org/wiki/Sugar_alcohol on Jan. 25, 2005.*
"Reducing Sugar" entry downloaded from http://en.wikipedia.org/wiki/Reducing_sugarl on Jan. 25, 2005.*
"Sugar" entry downloaded from http://en.wikipedia.org/wiki/Sugarl on Jan. 25, 2005.*

(Continued)

Primary Examiner—Alex Noguerola
(74) Attorney, Agent, or Firm—Amster, Rothstein & Ebenstein LLP (57) ABSTRACT

In a biosensor for measuring a specific substance in a liquid sample, one or a combination of sugar alcohol, metallic salt, organic acid or organic acid salt which has at least one carboxyl group in a molecule, and organic acid or organic acid salt which has at least one carboxyl group and one amino group in a molecule, is included in a reagent layer provided on electrodes, thereby providing a highly-accurate biosensor which is excellent in stability and has high response (sensitivity, linearity) of the sensor to the substrate concentration.

12 Claims, 7 Drawing Sheets

OTHER PUBLICATIONS

Trehalose entry obtained from ACS Registry on STN.*
Sucrose entry obtained from ACS Registry on STN.*
Glycerol entry obtained from ACS Registry on STN.*
Mannitol entry obtained from ACS Registry on STN.*
Ribose entry obtained from ACS Registry on STN.*
Sorbital entry obtained from ACS Registry on STN.*
Lactitol entry obtained from ACS Registry on STN.*
Maltitol entry obtained from ACS Registry on STN.*
JPO computer translation of JP 2000–081408 A (Yugawa et al.).*

* cited by examiner

BIOSENSOR

This application is the national stage under 35 U.S.C. 371 of International Application No. PCT/JP01/02558, filed on Mar. 28, 2001.

TECHNICAL FIELD

The present invention relates to a biosensor for analyzing a specific component in a liquid sample and, more particularly, to a reagent formulation for composing a reagent layer of the biosensor.

BACKGROUND ART

A biosensor is a sensor which utilizes the molecule identifying abilities of organic materials such as microorganisms, enzymes, and antibodies, and applies the organic materials as molecular recognition elements. That is, the biosensor utilizes a reaction which occurs when an immobilized organic material recognizes a target specific substance, such as oxygen consumption by respiration of a microorganism, an enzyme reaction, and luminescence.

Among biosensors, enzyme sensors have been put to practical use. For example, enzyme sensors for glucose, lactic acid, cholesterol, lactose, urea, and amino acid are utilized in medical measurement or food industry. An enzyme sensor reduces an electron acceptor by an electron generated by a reaction between a substrate included in a sample solution as a specimen and an enzyme, and a measuring device electrochemically measures the reduction quantity of the electron acceptor, thereby performing quantitative analysis of the specimen. As an example of such biosensor, a sensor proposed in Japanese Published Patent Application No. Hei. 11-1324511 has been known.

Figure 11:
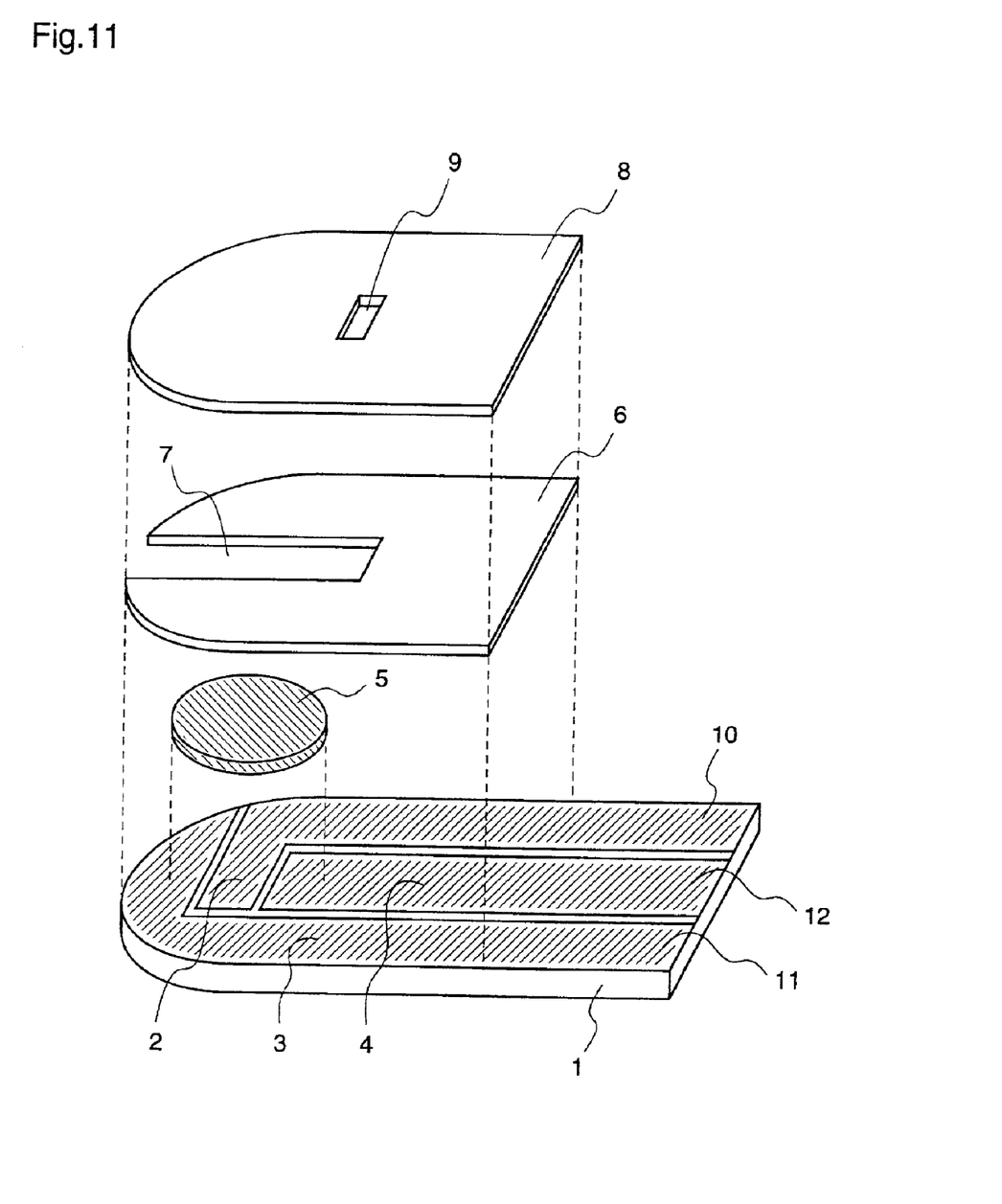
FIG. 11 exemplifies an exploded perspective view of a three-electrode-system biosensor.
Figure 12:
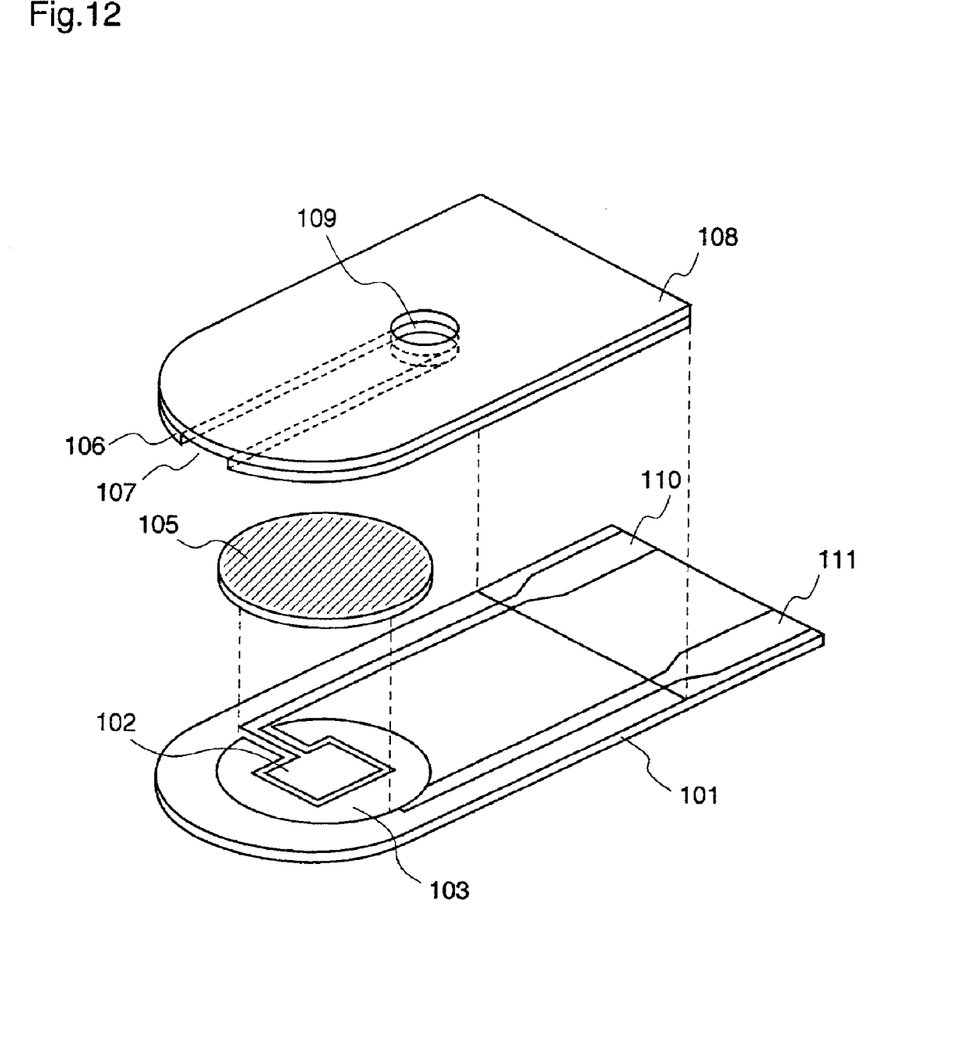
FIG. 12 exemplifies an exploded perspective view of a two-electrode-system biosensor.

FIGS. 11 and 12 are exploded perspective views illustrating conventional biosensors for measuring a blood sugar level. A measuring electrode 2 or 102 (also referred to as a working electrode), a counter electrode 3 or 103, and a detecting electrode 4, which electrodes comprise a conductive material, are formed on an insulating support 1 or 101 comprising polyethylene terephthalate or the like, and a reagent layer 5 or 105 including an enzyme which specifically reacts to a specific component in a sample solution, an electron transfer agent, and a hydrophilic polymer is formed on these electrodes.

In order to form a cavity for detecting an electric current value generated by a reaction between the specific component in the sample solution and a reagent in the reagent layer 5 or 105 with the above-mentioned electrodes 2, 3, 4, 102, 103, a spacer 6 or 106 having a spindly cutout pail 7 or 107 in a position on the electrodes and the reagent layer, and a cover 8 or 108 having an air vent 9 or 109 are attached onto the insulating support.

In the biosensor constructed as described above, the sample solution is supplied from the inlet of the cavity (sample suction inlet) to the inside of the cavity by capillary phenomenon and is let to the position of the electrodes and the reagent layer. When a specific component in the sample solution reacts to the reagent of the reagent layer, an electric current is generated, and the generated electric current is read by an external measuring device through leads of the biosensor, whereby quantitative analysis of the specimen is carried out.

However, in the biosensor with the above-described reagent composition, under the environment where heat and moisture exist, particularly under the environment of high temperature and humidity where the temperature is over 30° C. and the humidity is over 80%, a reduction reaction occurs between the electron transfer agent and a portion of enzyme protein or hydrophilic polymer which is included in the reagent layer 5 or 105, thereby generating a background electric current (noise electric current). As the value of the background electric current increases with time, the sensor performance is deteriorated.

Furthermore, as a means to solve the problem, it is possible to eliminate moisture and prevent the deterioration of the sensor performance by enclosing a desiccant such as silica gel or activated alumina into a biosensor preservation container which employs a molded container of resin or aluminium seal. However, it is impossible to completely eliminate water of molecular level remaining in the reagent included in the biosensor, with the desiccant alone.

Further, it is extremely hard to keep the preservation container free of moisture penetration over long term, and the reduction reaction between a portion of enzyme protein or hydrophilic polymer and the electron transfer agent is promoted when only a slight amount of moisture exists. Therefore, it is extremely difficult to effectively suppress the increase in the background electric current with time.

Further, when an inorganic salt such as potassium ferricyanide is included in the mixed reagent layer composed of various reagents such as an enzyme and an electron transfer agent, the reagent layer is extremely easily crystallized in the process of drying the reagent solution, whereby the surface of the reagent layer becomes rough and uneven, resulting in deterioration in the response (linearity, sensitivity) of the sensor to the substrate concentration and the measurement accuracy.

The present invention is made to solve the above-mentioned problems and has for its object to provide a highly-accurate biosensor which efficiently prevents deterioration of the performance of the biosensor due to contact with moisture, and has high response (linearity, sensitivity) of the sensor to the substrate concentration.

DISCLOSURE OF THE INVENTION

According to Claim 1 of the present invention, there is provided a biosensor for measuring the concentration of a specific substance in a sample solution, wherein sugar alcohol is included in a previously-provided reagent layer so that it is dissolved in the sample solution and specifically reacts to the specific substance in the sample solution. Therefore, it is possible to suppress an increase in a background electric current with time, and suppress a needles reaction with various contaminants existing in the blood, without preventing an enzyme reaction or the like, thereby providing a high-performance biosensor which is excellent in linearity (having a big slope and a small intercept of a regression expression) and has small variations among individual sensors.

According to Claim 2 of the present invention, in the biosensor as defined in Claim 1, the concentration of the specific substance is measured employing electrodes comprising at least a working electrode and a counter electrode provided on an insulating support. Therefore, it is possible to provide a biosensor which is suitable for an examination employing electrodes.

According to Claim 3 of the present invention, in the biosensor as defined in Claim 2, the reagent layer is formed on the electrodes or so that the electrodes are arranged in a diffusion area where a reagent in the reagent layer is dissolved and diffused in the sample solution, and the reagent layer includes at least an enzyme and an electron transfer agent. Therefore, it is possible to provide a biosensor which is suitable for an examination employing a reaction between an enzyme and an electron transfer agent.

According to Claim 4 of the present invention, in the biosensor as defined in any of Claims 1 to 3, the sugar alcohol is chain polyhydric alcohol or cyclic sugar alcohol, or a substitution product or derivative of the sugar alcohol. Claim 4 embodies the sugar alcohol defined in Claim 1 and, therefore, the same effect as in Claim 1 can be achieved.

According to Claim 5 of the present invention, in the biosensor as defined in any of Claims 1 to 3, the sugar alcohol is either or both of multiol and lactitol. Claim 5 embodies the sugar alcohol in Claim 1 and therefore, the same effects as in Claim 1 are achieved.

According to Claim 6 of the present invention, there is provided a biosensor for measuring the concentration of a specific substance in a sample solution, wherein metallic salt is included in a previously-provided reagent layer so that it is dissolved in the sample solution and specifically reacts to the specific substance in the sample solution. Therefore, it is possible to provide a biosensor which suppresses an increase in a background electric current with time, without preventing an enzyme reaction or the like.

According to Claim 7 of the present invention, in the biosensor as defined in Claim 6, the concentration of the specific substance is measured employing electrodes comprising at least a working electrode and a counter electrode provided on an insulating support. Therefore, it is possible to provide a biosensor which is suitable for an examination employing electrodes.

According to Claim 8 of the present invention, in the biosensor as defined in Claim 7, the reagent layer is formed on the electrodes or so that the electrodes are arranged in a diffusion area where a reagent in the reagent layer is dissolved and diffused in the sample solution, and the reagent layer includes at least an enzyme and an electron transfer agent. Therefore, it is possible to provide a biosensor which is suitable for an examination employing a reaction between an enzyme and an electron transfer agent.

According to Claim 9 of the present invention, in the biosensor as defined in any of Claims 6 to 8, the metallic salt is metallic salt sulfate, metallic salt hydrogensulfate, metallic salt sulfite, metallic salt hydrogensulfite, or metallic salt hyposulfite. Claim 9 embodies the metallic salt in Claim 6 and, therefore, the same effect as in Claim 6 is achieved.

According to Claim 10 of the present invention, in the biosensor as defined in any of Claims 6 to 8, the metallic salt is either or both of magnesium sulfate and calcium sulfate. Claim 10 embodies the metallic salt in Claim 6 and, therefore, the same effect as in Claim 6 is achieved.

According to Claim 11 of the present invention, in the biosensor as defined in any of Claims 6 to 8, the metallic salt is metallic salt nitrate, metallic salt hydrogennitrate, metallic salt nitrite, metallic salt hydrogennitrite, or metallic salt hyponitrite. Claim 11 embodies the metallic salt in Claim 6 and, therefore, the same effect as in Claim 6 is achieved.

According to Claim 12 of the present invention, in the biosensor as defined in any of Claims 6 to 8, the metallic salt is either or both of magnesium nitrate and calcium nitrate. Claim 12 embodies the metallic salt in Claim 6 and, therefore, the same effect as in Claim 6 is achieved.

According to Claim 13 of the present invention, there is provided a biosensor for measuring the concentration of a specific substance in a sample solution, wherein organic acid or organic acid salt which has at least one carboxyl group in its molecule is included in a previously-provided reagent layer so that it is dissolved in the sample solution and specifically reacts to the specific substance in the sample solution. Therefore, it is possible to suppress an increase in a background electric current with time, and suppress a needles reaction with various contaminants existing in the blood, without preventing an enzyme reaction or the like, thereby providing a high performance biosensor which is excellent in linearity (having a big slope and a small intercept of a regression expression) and has small variations among individual sensors.

According to Claim 14 of the present invention, in the biosensor as defined in Claim 13, the concentration of the specific substance is measured employing electrodes comprising at least a working electrode and a counter electrode provided on an insulating support. Therefore, it is possible to provide a biosensor which is suitable for an examination employing electrodes.

According to Claim 15 of the present invention, in the biosensor as defined in Claim 14, the reagent layer is formed on the electrodes or so that the electrodes are arranged in a diffusion area where a reagent in the reagent layer is dissolved and diffused in the sample solution, and the reagent layer includes at least an enzyme and an electron transfer agent. Therefore, it is possible to provide a biosensor which is suitable for an examination employing a reaction between an enzyme and an electron transfer agent.

According to Claim 16 of the present invention, in the biosensor as defined in any of Claims 13 to 15, the organic acid is aliphatic carboxylic acid, carbocyclic carboxylic acid, or heterocyclic carboxylic acid, or a substitution product or derivative of the organic acid. Claim 19 embodies the organic acid in Claim 13 and, therefore, the same effect as in Claim 13 is achieved.

According to Claim 17 of the present invention, in the biosensor as defined in any of Claims 13 to 15, the carboxylic acid is one of glutaric acid, adipic acid, phthalic acid, and benzoic acid, or a combination of these acids. Claim 17 embodies the carboxylic acid in Claim 13 and, therefore, the same effect as in Claim 13 is achieved.

According to Claim 18 of the present invention, there is provided a biosensor for measuring the concentration of a specific substance in a sample solution, wherein organic acid or organic acid salt which has at least one carboxyl group and one amino group in its molecule is included in a previously-provided reagent layer so that it is dissolved in the sample solution and specifically reacts to the specific substance in the sample solution. Therefore, it is possible to form the reagent layer closely and homogeneously packed, thereby providing a biosensor which can dramatically enhance a response (sensitivity, linearity) of the sensor to the substrate concentration.

According to Claim 19 of the present invention, in the biosensor as defined in Claim 18, the concentration of the specific substance is measured employing electrodes comprising at least a working electrode and a counter electrode provided on an insulating support. Therefore, it is possible to provide a biosensor which is suitable for an examination employing electrodes.

According to Claim 20 of the present invention, in the biosensor as defined in Claim 19, the reagent layer is formed on the electrodes or so that the electrodes are arranged in a diffusion area where a reagent in the reagent layer is dissolved and diffused in the sample solution, and the reagent layer includes at least an enzyme and an electron transfer agent. Therefore, it is possible to provide a biosensor which is suitable for an examination employing a reaction between enzyme and an electron transfer agent.

According to Claim 21 of the present invention, in the biosensor as defined in any of Claims 18 to 20, the organic acid is amino acid, or a substitution product or derivative of the amino acid. Claim 21 embodies the organic acid in Claim 18 and, therefore, the same effect as in Claim 18 is achieved.

According to Claim 22 of the present invention, in the biosensor as defined in any of Claims 18 to 20, the amino acid is one of glycine, serine, proline, threonine, lysine, and taurine, or a combinaiton of these acids. Claim 22 embodies the amino acid in Claim 18 and, therefore, the same effect as in Claim 18 is achieved.

According to Claim 23 of the present invention, there is provided a biosensor for measuring the concentration of a specific substance in a sample solution, wherein a combination of at least two of sugar alcohol, metallic salt, organic acid or organic acid salt which has at least one carboxyl group in its molecule, and organic acid or organic acid salt which has at least one carboxyl group and one amino group in its molecule, is included in a previously-provided reagent layer so that it is dissolved in the sample solution and specifically reacts to the specific substance in the sample solution. Therefore, it is possible to provide a highly-accurate biosensor which is excellent in stability and has high response (sensitivity, linearity) of the sensor to the substrate concentration.

According to Claim 24 of the present invention, in the biosensor as defined in any of Claims 1 to 23, the reagent layer further includes a hydrophilic polymer. Since the reagent layer includes the hydrophilic polymer, formation of homogeneous reagent on the surface of the electrodes is facilitated, and adhesion between the electrodes and the reagent is enhanced. Further, since the respective substances are homogeneously dispersed in the reagent layer, homogeneous reagent formation can be realized, thereby providing a high performance biosensor which has small variations among individual sensors.

BEST MODE TO EXECUTE THE INVENTION (Embodiment 1)

Hereinafter, a biosensor according to a first embodiment of the present invention will be described. In the respective embodiments of the invention described below, an enzyme sensor, which employs an enzyme as a molecular recognition element that specifically reacts to a specific substance in a sample solution, is exemplified.

FIG. 11 exemplifies an exploded perspective view of a three-electrode-system biosensor, and FIG. 12 exemplifies an exploded perspective view of a two-electrode-system biosensor. In FIGS. 11 and 12, numeral 1 or 101 denotes an insulating support, on which a working electrode 2 or 102 and a counter electrode 3 or 103 are formed at prescribed positions in prescribed shapes. Further, in the three-electrode-system biosensor shown in FIG. 11, a detecting electrode 4 is formed on the insulating support 1 at a prescribed position in a prescribed shape. The detecting electrode 4 here serves as an electrode for detecting shortage of a specimen quantity and, further, it can be employed as a part of a reference electrode or the counter electrode.

Preferably, a material of the insulating support 1 or 101 is polyethylene terephthalate, polycarbonate, polyimide, or the like.

Further, a conductive substance constituting each electrode is a simple substance such as a carbon or a noble metal such as gold, platinum, palladium, or the like, or a compound material such as a carbon paste or a noble-metal paste.

The simple substance such as carbon or noble metal such as gold, platinum, palladium, or the like can be easily formed into a conductive layer on the insulating support 1 or 101 employing spattering deposition or the like, and the compound material such as a carbon paste or a noble-metal paste can be easily formed into a conductive layer on the insulating support 1 or 101 employing screen printing or the like.

In the formation of the respective electrodes, the conductive layer is formed over the entire or partial insulating support 1 or 101 by the above-mentioned spattering deposition or screen printing and, thereafter, slits are formed 11 using a laser or the like to divide the conductive layer into the respective electrodes. Further, the electrodes can be similarly formed by screen printing or spattering deposition employing a printing plate or a mask plate on which an electrode pattern is previously formed.

A reagent layer 5 or 105, which includes an enzyme, an electron transfer agent, a hydrophilic polymer, and sugar alcohol, is formed on the electrodes formed as described above.

The first embodiment of the invention is characterized by that the sugar alcohol is included in the reagent layer 5 or 105, and the sugar alcohol prevents that the oxidized-form electron transfer agent gets contact with a part of a reactive functional group existing in enzyme protein or hydrophilic polymer included in the reagent, so that the electron transfer agent is denatured (reduced) from the oxidized-form to reduced-form in the reagent layer 5 or 105 formed on the electrodes.

Accordingly, in the biosensor with the above-described reagent formulation, under the environment where heat and moisture exist, particularly under the environment of high temperature and humidity where the temperature is over 30° C. and the humidity is over 80%, it is possible to suppress a background electric current (noise electric current) which occurs due to a reduction reaction between the electron transfer agent and a part of enzyme protein or hydrophilic polymer included in the reagent layer 5 or 105, and is increased with time, thereby preventing the performance of the biosensor from being deteriorated.

Further, since the sugar alcohol is included in the reagent layer, a needles reaction with various contaminants existing in the blood, especially in blood corpuscles, can be also suppressed, thereby providing high performance biosensors which are excellent in linearity (having a big slope and a small segment of a regression expression) and have less variations among the individual sensors.

The sugar alcohol included in the reagent layer 5 or 105 may be chain polyhydric alcohol or cyclic sugar alcohol such as sorbitol, maltitol, xylitol, mannitol, lactitol, reduced paratinose, arabinitol, glycerol, ribitol, galactitol, sedoheptitol, perseitol, boremitol, styratitol, polygalitol, iditol, talitol, allitol, ishylitol, reduced starch saccharified material, and ishylitol.

The same effect as above can also be achieved by using the stereoisomer, substitution product, or derivative of any of the sugar alcohols.

Among these sugar alcohols, maltitol and lactitol are the most suitable material since they are relatively low in the unit price, are easily available, and are highly effective in suppressing the background electric current.

The addition quantity of the sugar alcohol is preferably 0.1–500 mM as the reagent solution concentration, and more preferably, 1–100 mM.

Thereafter, in the biosensor as shown in FIG. 11 or 12, the spacer 6 or 106 having the cutout part 7 or 107 and the cover 8 or 108 are attached onto the reagent layer 5 or 105 and the electrodes 2, 3, 4, 102, 103, whereby a cavity through which the sample solution is supplied is formed.

A material suitable for the spacer 6 or 106 and the cover 8 or 108 may be polyethylene terephthalate, polycarbonate, polyimide, polybutylene terephthalate, polyamide, polyvinyl chloride, polyvinylidene chloride, nylon, and the like.

The supply of the sample solution to the biosensor having such cavity is realized by capillary phenomenon, and an air vent 9 or 109 for letting air out of the biosensor is required in the cavity for smooth supply of the sample solution.

The air vent 9 or 109 can be arranged at any position in the cavity unless it prevents the supply of the sample solution.

In the so-formed biosensor, the electric current value obtained by the reaction between a specific component in the sample solution and the reagent layer 5 or 105 including an enzyme or the like is read by an external measuring device connected through lead parts 10, 11, 12, 110, 111 of the working electrodes 2 or 102, the counter electrode 3 or 103, and the detecting electrode 4.

(Embodiment 2)

Hereinafter, a biosensor according to a second embodiment of the present invention will be described.

The biosensor according to the second embodiment of the invention is the biosensor shown in FIG. 11 or 12 whose reagent layer 5 or 105 is formed of an enzyme, an electron transfer agent, a hydrophilic polymer, and a metallic salt. Other constituents are the same as those of the above-described biosensor according to the first embodiment and, therefore, descriptions thereof will be omitted.

The second embodiment of the invention is characterized by that a metallic salt is included in the reagent layer 5 or 105, and the metallic salt prevents that the oxidized-form electron transfer agent gets contact with a part of a reactive functional group existing in enzyme protein and hydrophilic polymer included in the reagent, so that the electron transfer agent is denatured (reduced) from the oxidized form to reduced form in the reagent layer 5 or 105 formed on the electrodes.

Accordingly, in the biosensor with the above-described reagent constitution, under the environment where heat and moisture exist, particularly under the environment of high temperature and humidity where the temperature is over 30° C. and the humidity is over 80%, it is possible to suppress a background electric current (noise electric current) which occurs due to the reduction reaction between the electron transfer agent and a part of enzyme protein or hydrophilic polymer and is increased with time, thereby preventing the performance of the biosensor from being deteriorated.

As the metallic salt included in the reagent layer 5 or 105, metallic salt sulfate or metallic salt nitrate is particularly effective. As metallic salt sulfate, metallic salt hydrogensulfate, metallic salt sulfite, metallic salt hydrogensulfite, or metallic salt hyposulfite, for example, there are aluminium sulfate, magnesium sulfate, zinc sulfate, antimony sulfate, indium sulfate, uranyl sulfate, uranium sulfate, cadmium sulfate, potassium sulfate, gallium sulfate, calcium sulfate, silver sulfate, chromium sulfate, cobalt sulfate, potassium bisulfate, zirconium sulfate, mercury sulfate, tin sulfate, strontium sulfate, caesium sulfate, cerium sulfate, thallium sulfate, titanium sulfate, iron sulfate, copper sulfate, sodium sulfate, lead sulfate, nickel sulfate, neodymium sulfate, vanadium sulfate, palladium sulfate, barium sulfate, bismuth sulfate, praseodymium sulfate, beryllium sulfate, manganese sulfate, lanthanum sulfate, lithium sulfate, rubidium sulfate, aluminium potassium sulfate, aluminium sodium sulfate, uranyl potassium sulfate, potassium chromium sulfate, disodium magnesium sulfate, magnesium dipotassium sulfate, manganese caesium sulfate, rubidium aluminium sulfate, potassium hydrogensulfate, sodium hydrogensulfate, potassium sulfite, calcium sulfite, sodium sulfite, barium sulfite, bismuth sulfite, sodium hyposulfite, potassium bisulfite, sodium bisulfite, and the like, while, as metallic salt nitrate, metallic salt hydrogennitrate, metallic salt nitrite, metallic salt hydrogennitrite, or metallic salt hyponitrite, there are aluminium nitrate, magnesium nitrate, zinc nitrate, antimony sulfate, ytterbium nitrate, yttrium nitrate, indium nitrate, uranyl nitrate, erbium nitrate, cadmium nitrate, gadolinium nitrate, potassium nitrate, calcium nitrate, silver nitrate, chromium nitrate, cobalt nitrate, samarium nitrate, zirconium nitrate, dysprosium nitrate, mercury nitrate, tin nitrate, strontium nitrate, caesium nitrate, cerium nitrate, thallium nitrate, iron nitrate, terbium nitrate, copper nitrate, thorium nitrate, sodium nitrate, lead nitrate, nickel nitrate, neodymium nitrate, palladium nitrate, barium nitrate, bismuth nitrate, praseodymium nitrate, beryllium nitrate, holmium nitrate, manganese nitrate, europium nitrate, lanthanum nitrate, lithium nitrate, ruthenium nitrate, rubidium nitrate, rhodium nitrate, thallium mercury nitrate, potassium nitrite, silver nitrite, calcium nitrite, sodium nitrite, potassium cobaltinitrite, sodium cobaltinitrite, sodium hyponitrite, and the like.

Among these metallic salts, magnesium sulfate, calcium sulfate, magnesium nitrate, and calcium nitrate are particularly suitable because they are highly effective in preventing moisture absorption.

The addition quantity of the metallic salt is suitably 0.1–500 mM as a reagent solution concentration, and more suitably, 1–50 mM.

(Embodiment 3)

Hereinafter, a biosensor according to a third embodiment of the present invention will be described.

The biosensor according to the third embodiment of the invention has a reagent layer 5 or 105 shown in FIG. 11 or 12, which is formed of an enzyme, an electron transfer agent, a hydrophilic polymer, and an organic acid or organic acid salt which has at least one carboxyl group in a molecule. Other constituents are the same as those of the above-described biosensor according to the first embodiment and, therefore, descriptions thereof will be omitted.

The third embodiment of the invention is characterized by that an organic acid or organic acid salt having at least one carboxyl group in a molecule is included in the reagent layer 5 or 105, and the organic acid or organic acid salt prevents that the oxidized-form electron transfer agent gets contact with a part of a reactive functional group existing in enzyme protein and hydrophilic polymer included in the reagent, so that the electron transfer agent gets denatured (reduced) from the oxidized form to reduced form in the reagent layer 5 or 105 formed on the electrodes.

Accordingly, in the biosensor with the above-described reagent constitution, under the environment where heat and moisture exist, particularly under the environment of high temperature and humidity where the temperature is over 30° C. and the humidity is over 80%, it is possible to suppress a background electric current (noise electric current) which occurs due to the reduction reaction between a part of enzyme protein or hydrophilic polymer and the electron transfer agent and is increased with time, thereby preventing the performance of the biosensor from being deteriorated.

Further, since the organic acid or organic acid salt having at least one carboxyl group in a molecule is included in the reagent layer, a needles reaction with various contaminants existing in the blood, particularly in blood corpuscles, can be also suppressed, thereby providing high performance biosensors which are excellent in linearity (having a big slope and a small intersept of a regression expression) and have less variations among individual sensors.

The organic acid or organic acid salt which has at least one carboxyl group in a molecule and is included in the reagent layer 5 or 105 may be aliphatic carboxylic acid, carbocyclic carboxylic acid, heterocyclic carboxylic acid, or their salt.

For example, the aliphatic carboxylic acid may be malonic acid, succinic acid, glutaric acid, adipic acid, maleic acid, fumaric acid, and their salt.

The degree of the effect becomes larger as the straight chain is longer and the molecular weight is larger, and particularly, an organic acid or organic acid salt having three or more hydrocarbon chains is desirable. Further, as for a reagent employed for the biosensor, a reagent having more hydrophilic functional groups in the molecular structure is preferable since the reagent is required to be highly soluble in water.

Further, the carbocyclic carboxylic acid may be benzoic acid, phthalic acid, isophthalic acid, terephthalic acid, and their salt, and the same effect as the above can be obtained by employing these.

The heterocyclic carboxylic acid may be 2-phthalic-acid, nicotinic acid, isonicotinic acid, and their salt, and the same effect as the above can be obtained by employing these.

Further, in addition to the above-described aliphatic and carbocyclic carboxylic acid, as well as heterocyclic carboxylic acid or carboxylate salt, malic acid, oxaloacetic acid, citric acid, ketoglutaric acid, and their salt, for example, in which functional groups of the carboxylic acid or carboxylate salt are partially replaced by other functional groups, can also achieve the same effect as described above.

Among such organic acids or organic acid salts, glutaric acid, adipic acid, phthalic acid, and benzoic acid are most suitable.

The addition quantity of the organic acid or organic acid salt is suitably 0.01–100 mM as a reagent solution concentration and, more suitably, 0.1–10 mM.

(Embodiment 4)

Hereinafter, a biosensor according to a fourth embodiment of the present invention will be described.

The biosensor according to the fourth embodiment of the invention has a reagent layer 5 or 105 shown in FIG. 11 or 12, which is formed of an enzyme, an electron transfer agent, a hydrophilic polymer, and an organic acid or organic acid salt which has at least one carboxyl group and one amino group in a molecule. Other constituents are the same as those of the above-described biosensor according to the first embodiment and, therefore, descriptions thereof will be omitted.

The fourth embodiment of the invention is characterized by the an organic acid or organic acid salt having at least one carboxyl group and one amino group in a molecule is included in the reagent layer 5 or 105, and addition of the organic acid or organic acid salt into the reagent layer 5 or 105 provides the effect that the surface state of the reagent layer 5 or 105 can be made extremely smooth and homogeneous. Although the reagent layer 5 or 105 is easily crystallized in the process of drying the reagent solution when inorganic salt such as potassium ferricyanide employed as an electron transfer agent is included in the reagent layer, the crystallization of the inorganic salt can be prevented by the organic acid or organic acid salt which has at least one carboxyl group and one amino group in a molecule and is included in the reagent.

Since the inorganic salt prevented from being crystallized exists in the reagent layer as a particulate, it can get close and uniform contact with an enzyme molecule, resulting in a reagent layer condition which is excellent in efficiency of electron transfer with the enzyme molecule.

Further, since the solubility of the reagent layer can be enhanced, the sensitivity and linearity of the sensor can be dramatically improved.

The organic acid or organic acid salt, which has at least one carboxyl group and one amino group in a molecule and is included in the reagent layer 5 or 105, may be an organic acid or organic acid salt such as glycine, alanine, valine, leucine, isoleucine, serine, threonine, methionine, asparagine, glutamine, arginine, lysine, histidine, phenylalanine, tryptophan, proline, or their salt, or sarcosine, betaine, taurine, or the like.

The same effect as above can be achieved by employing the substitution product or derivative of any of these organic acids or organic acid salts.

Among the organic acids or organic acid salts, glycine, serine, proline, threonine, lysine, and taurine are particularly suitable since they are effective in preventing crystallization.

The addition quantity of the organic acid or organic acid salt is suitably 0.1–100 mM as a reagent solution concentration and, more suitably, 10–500 mM.

In the first to fourth embodiments of the invention, descriptions are given of the cases where sugar alcohol, metallic salt, organic acid or organic acid salt which has at least one carboxyl group in a molecule, and organic acid or organic acid salt which has at least one carboxyl group and one amino group in a molecule are respectively added to the reagent layer 5 or 105, these additives may be appropriately combined.

The enzyme, which is included in the reagent in the first to fourth embodiments of the invention, may be glucose oxidase, lactate oxidase, cholesterol oxidase, cholesterol esterase, uricase, ascorbia acid oxidase, bilirubin oxidase, glucose dehydrogenase, lactate dehydrogenase, or the like, and the electron transfer agent may be potassium ferricyanide, p-benzoquinone or its derivative, phenazine methosulfate, methylene blue, ferrocene or its derivative, or the like.

In the first to fourth embodiments of the invention, the reagent layer 5 or 105 includes a hydrophilic polymer, whereby the sample solution has a viscosity, and the formation of the reagent on the electrodes is facilitated and homogenized and, further, the adhesion between the electrodes and the reagent is enhanced. Furthermore, the hydrophilic polymer included in the reagent layer makes the condition of the reagent crystal after the reagent is dried even and homogeneous, resulting in a high-accurate biosensor.

Hydrophilic polymers used for the above-described purpose may be carboxymethyl cellulose, hydroxyethyl cellulose, hydroxypropylcellulose, methyl cellulose, ethyl cellulose, ethyl hydroxyethyl cellulose, carboxymethyl ethyl cellulose, polyvinyl alcohol, polyvinyl pyrrolidone, polyamino acid such as polylysine, polystyrene sulfonate, or gelatine and its derivative, acrylic acid and its salt, methacrylic acid and its salt, starch and its derivative, maleic anhydride and its salt, and agarose gel and its derivative.

While in the first to fourth embodiments of the invention the above-described reagent layer 5 or 105 is provided on the electrodes, specifically the reagent layer 5 or 105 can be arranged over the entire surface or part of the electrodes. Besides, the reagent layer 5 or 105 may be arranged within a range where the performance of the biosensor is not deteriorated, i.e., a range where the electrodes are provided within an area in which the reagent in the reagent layer is dissolved and diffused into the sample solution.

EXAMPLE 1

A palladium thin film of approximately 10 nm thick is formed over the entire surface of an insulating support comprising polyethylene terephthalate by spattering deposition and, thereafter, slits are formed in part of the thin film using a YAG laser so as to divide the thin film into a working electrode, a counter electrode, and a detecting electrode. On the electrodes, an aqueous solution including an enzyme (glucose oxidase), an electron transfer agent (potassium ferricyanide), a hydrophilic polymer (carboxymethyl cellulose), and sugar alcohol is circularly dropped centering around the working electrode so as to cover parts of the counter electrode and the detecting electrode, and then it is dried, thereby forming a reagent layer. On the reagent layer, a spacer having a cutout part and comprising polyethylene terephthalate and a cover having an air vent and comprising polyethylene terephthalate are attached, thereby manufacturing a three-electrode-system sensor for measuring a blood sugar level, in which a cavity as a capillary for leading blood is formed.

Figure 1:
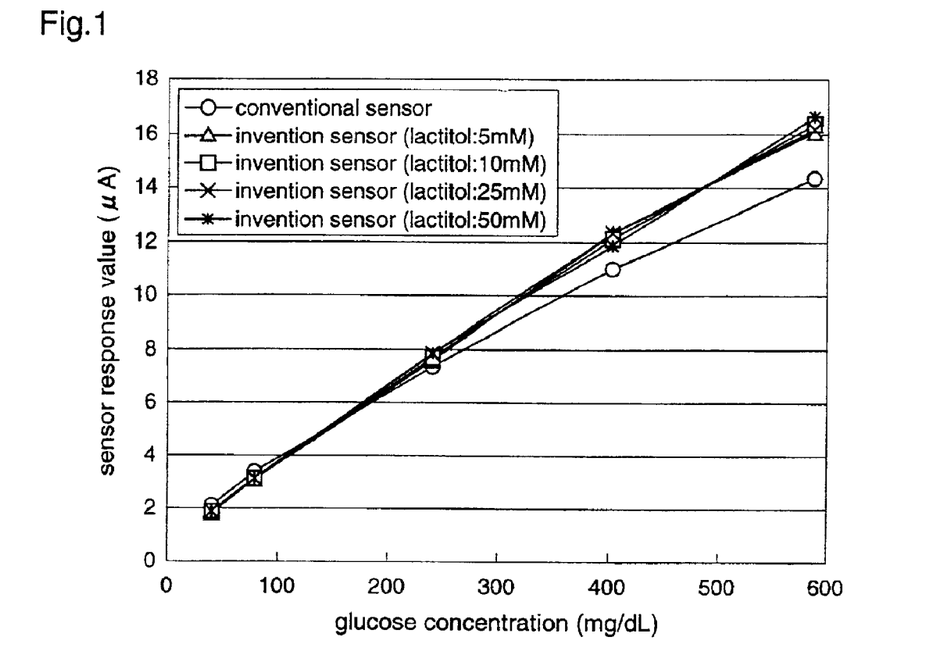
FIG. 1 is a diagram illustrating sensor response characteristics when lactitol is added as sugar alcohol into a reagent solution, in a first embodiment.
Figure 2:
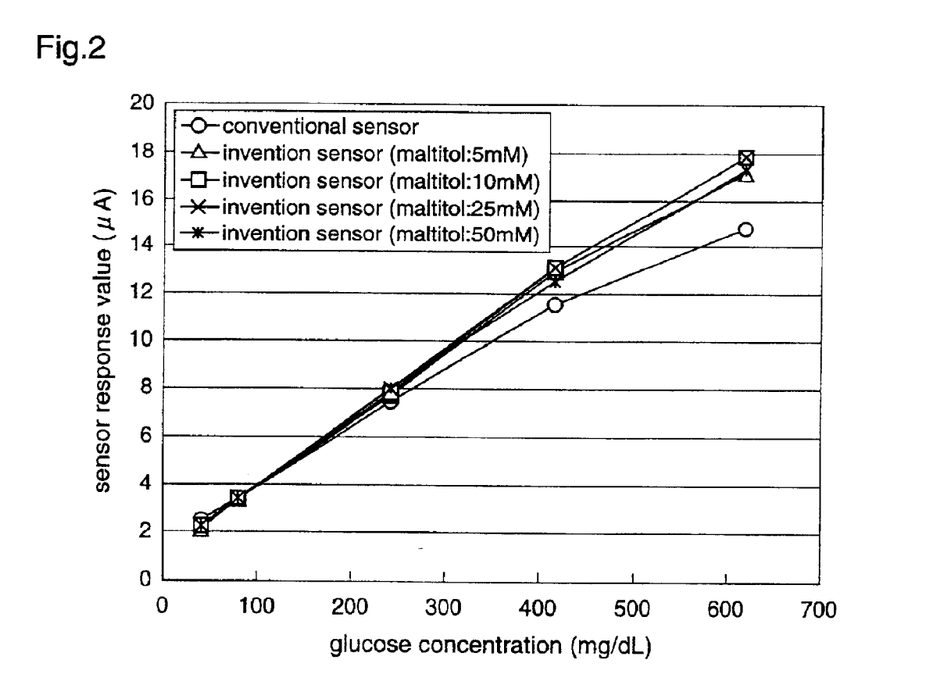
FIG. 2 is a diagram illustrating sensor response characteristics when maltitol is added as sugar alcohol into the reagent solution, in the first embodiment.

FIG. 1 illustrates sensor response characteristics when lactitol is added into the reagent solution as sugar alcohol, in the case where the sample solution is whole blood and the lactitol concentration is varied in four levels. Likewise, FIG. 2 illustrates sensor response characteristics in the case where maltitol is added as sugar alcohol and the maltitol concentration is varied in four levels. Here, a sensor in which the sugar alcohol addition concentration (the concentration as a sample aqueous solution) is 0 is handled as a conventional sensor, and sensors in which the sugar alcohol addition concentrations are 5, 10, 25, and 50 mM are employed as invention sensors.

Figure 3:
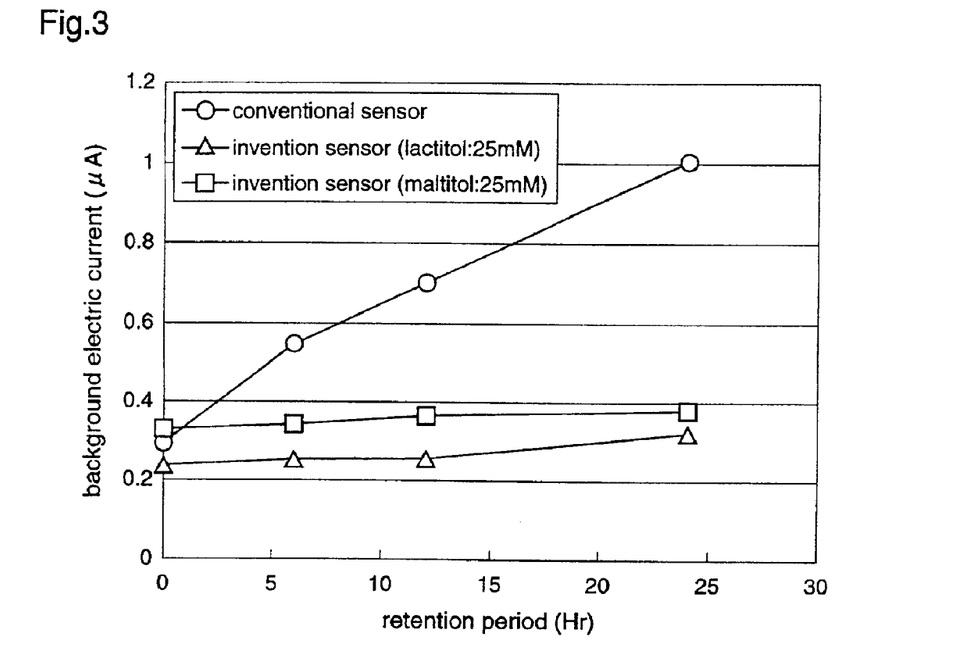
FIG. 3 is a diagram illustrating an increase in the background electric current under a harsh environment when purified water is employed as a sample solution in the first embodiment.
Figure 4:
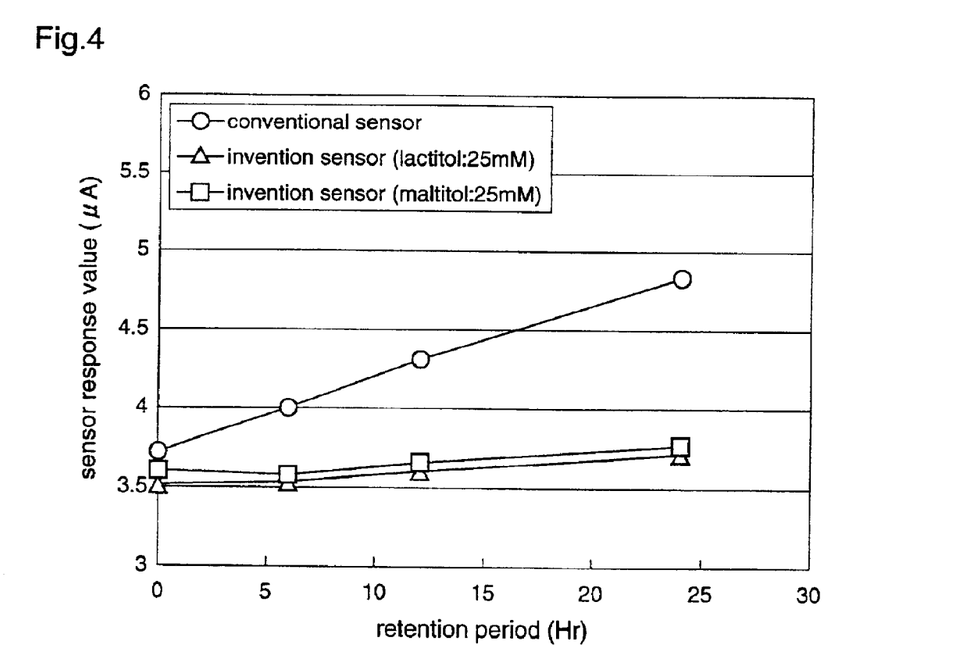
FIG. 4 is a diagram illustrating an increase in the whole blood response value under a harsh environment when the whole blood is employed as the sample solution in the first embodiment.

FIG. 3 illustrates change of a background electric current value with time under a harsh environment (exposure in temperature of 30° C. and humidity of 80%), which is measured using the sensor manufactured as described above. Purified water including no glucose is employed as a sample solution. FIG. 4 illustrates change of a sensor response value with time in the case where whole blood adjusted to have the glucose concentration of 80 mg/dL is employed as a sample solution. In either case, there are four points of measurement in total: just after the sensor is manufactured (0-hour), 6-hour, 12-hour, and 24-hour after the manufacture.

The current measurement condition is as follows. After confirming that the cavity is filled with the sample solution, enzyme reaction is promoted for twenty-five seconds. Thereafter, a voltage of 0.2V is applied among the working electrode, the counter electrode, and the detecting electrode, and an electric current value obtained five seconds after the application is measured. Here, the detecting electrode is also employed as a part of the counter electrode.

The number of measurement n is n=10 for each concentration and measurement time, and the average thereof is plotted in the figures.

As is evident from FIG. 1, the response characteristics of the sensor in which lactitol is added as sugar alcohol tend to be high particularly in a range where the glucose concentration is high, i.e., over 400 mg/dL, as compared with the conventional sensor including no sugar alcohol, and this result indicates that excellent response characteristics with a favorable regression expression (having a small intercept and a big slope) are obtained.

As is evident from FIG. 2, also when maltitol is employed as sugar alcohol, excellent response characteristics are obtained as in the above-mentioned case of employing lactitol.

Furthermore, as is evident from FIGS. 3 and 4, in the sensor to which the sugar alcohol is added, increase in the background electric current in the exposure environment under the high temperature and humidity is efficiently suppressed, resulting in excellent preservation stability with small variations of the sensor response value with time.

EXAMPLE 2

A sensor for measuring a blood sugar level is manufactured by the same procedure as in the first example. In this second example, magnesium sulfate as metallic salt sulfate is added instead of sugar alcohol as an addition agent for suppressing increase of a background electric current with time.

Figure 5:
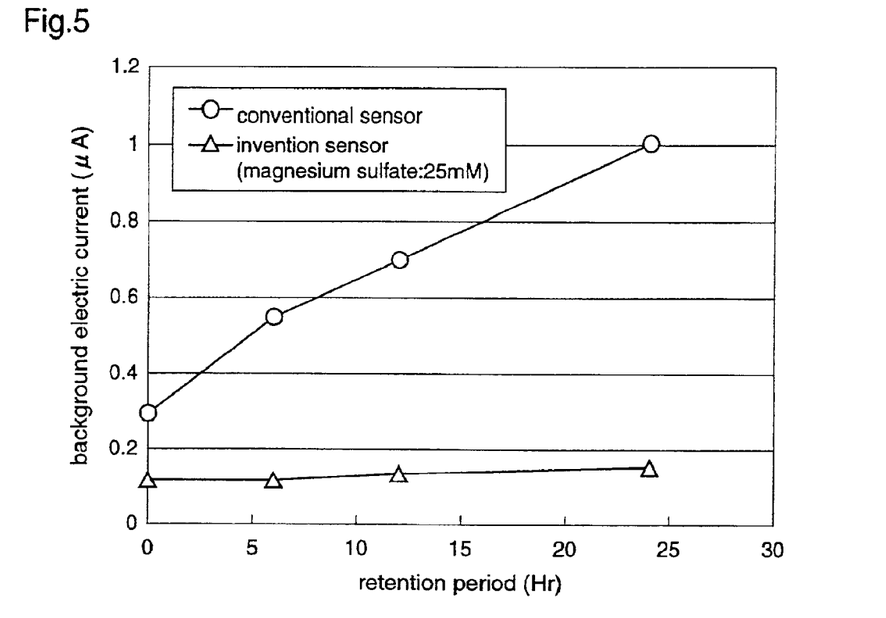
FIG. 5 is a diagram illustrating an increase in the background electric current under a harsh environment when purified water is employed as a sample solution in a second embodiment.
Figure 6:
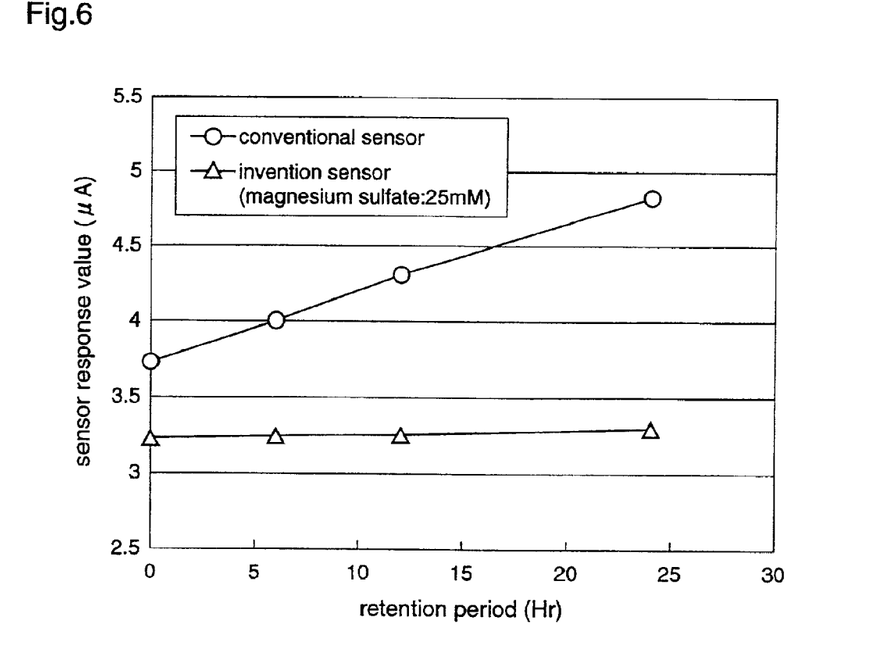
FIG. 6 is a diagram illustrating an increase in the whole blood response value under a harsh environment when the whole blood is employed as the sample solution in the second embodiment.

FIG. 5 illustrates change of a background electric current value with time under a harsh environment (exposure in temperature of 30° C. and humidity of 80%), which is measured employing the sensor manufactured as described above. Purified water including no glucose is employed as a sample solution. FIG. 6 illustrates change of a sensor response value with time in the case where whole blood adjusted to have the glucose concentration of 80 mg/dL is employed as a sample solution.

In either case, there are four points of measurement in total: just after the sensor is manufactured (0-hour), 6-hour, 12-hour, and 24-hour after the manufacture.

The number of measurement n is the same as that in the first example.

As is evident from FIGS. 5 and 6, also in the sensor in which metallic salt sulfate is added, as well as sugar alcohol in the first example, increase in the background electric current in the exposure environment under the high temperature and humidity is efficiently suppressed, resulting in excellent preservation stability with small variations of the sensor response value with time.

EXAMPLE 3

An electrode layer comprising a working electrode and a counter electrode is formed on an insulating support comprising polyethylene terephthalate by screen printing, and a reagent layer including an enzyme (glucose oxidase), an electron transfer agent (potassium ferricyanide), a hydrophilic polymer (carboxymethyl cellulose), and aliphatic carboxylic acid (concentration of which is 5 mM as a sample solution) is formed on the electrode layer. Thereafter, a spacer comprising polyethylene terephthalate and a cover also comprising polyethylene terephthalate are attached, thereby manufacturing a two-electrode-system sensor for measuring a blood sugar level, in which a cavity as a capillary for leading blood is formed.

Here, four kinds of two-electrode-system sensors in total are manufactured: three sensors respectively including, as organic acids, malonic acid (HOOC—$CH_2$—COOH) as aliphatic carboxylic acid, glutaric acid (HOOC—$CH_2$—$CH_2$—$CH_2$—COOH), and adipic acid (HOOC—$CH_2$—$CH_2$—$CH_2$—$CH_2$—COOH), and a conventional sensor including no aliphatic carboxylic acid.

Figure 7:
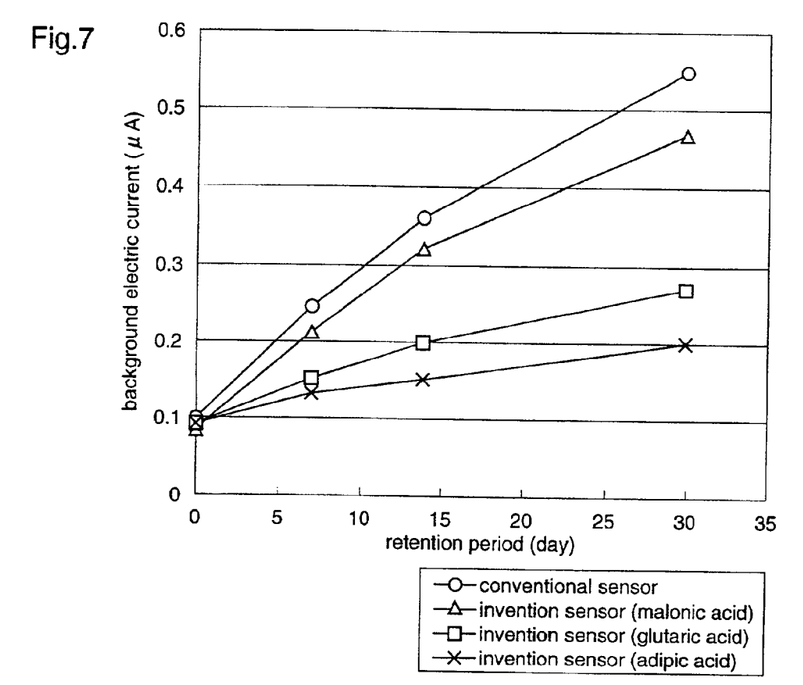
FIG. 7 is a diagram illustrating an increase in the background electric current under a harsh environment when purified water is employed as a sample solution in a third embodiment.

FIG. 7 illustrates background electric currents under a harsh environment (temperature of 40° C. and humidity of 80%), which are measured employing the four sensors manufactured as mentioned above. Purified water including no glucose is employed as a sample solution. There are four points of measurement in total: just after the sensor is manufactured (0-hour), 7-day, 14-day, and 30-day after the manufacture. The measurement condition is as follows. The cavity is filled with the sample solution (purified water), and the reaction is promoted for twenty-five seconds. Thereafter, a voltage of 0.5V is applied between the working electrode and the counter electrode, and an electric current value obtained five seconds after the application is measured.

The number of measurement n is n=10 for each measurement point, and the average thereof is plotted in FIG. 7.

As is evident from FIG. 7, increase in the background electric current is reliably suppressed in the sensors added with the aliphatic carboxylic acids, and the pace of the increase is reduced in the order of malonic acid, glutaric acid, and adipic acid, thereby suggesting that the sensor with more complicated molecular structure, longer straight chain, and larger molecular weight is more effective in suppressing the increase in the background electric current. The electric current value thus obtained corresponds to the quantity of potassium ferrocyanide which is generated by a reaction between glucose oxidase and potassium ferricyanide as well as carboxymethyl cellulose and potassium ferricyanide.

EXAMPLE 4

A biosensor is manufactured by the same procedure as in the third example and the same evaluation as in the third example is made. This fourth example employs three kinds of organic acids as follows: benzoic acid and phthalic acid as carbocyclic carboxylic acids, and malic acid (derivative of succinic acid) with the structure in which a part of hydrocarbon chain of succinic acid is replaced by a hydroxyl group.

Figure 8:
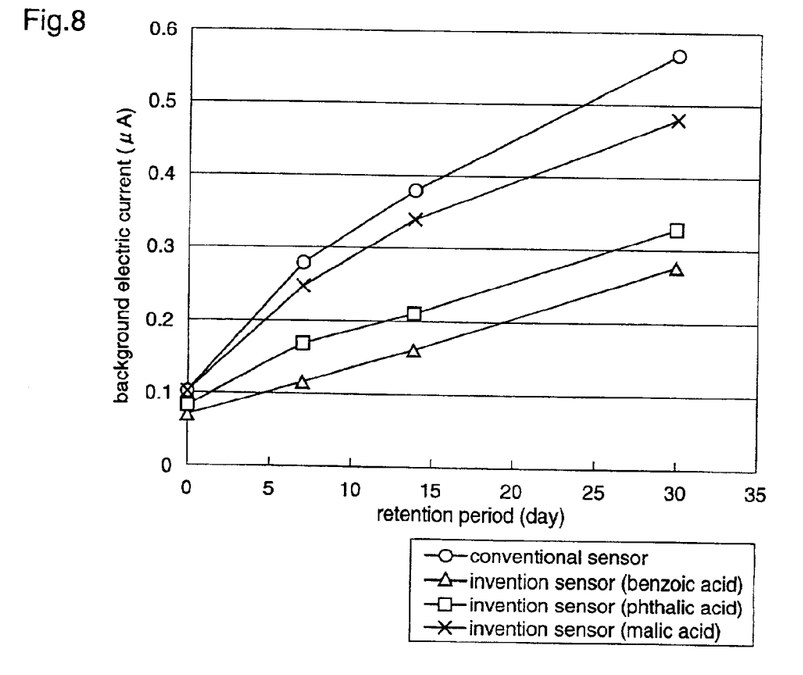
FIG. 8 is a diagram illustrating an increase in the background electric current under a harsh environment when purified water is employed as a sample solution in a fourth embodiment.

As is evident from FIG. 8, the effect of suppressing increase in the background electric current is confirmed whichever organic acid of benzoic acid, phthalic acid, or malic acid is employed as in the third example.

EXAMPLE 5

An electrode layer comprising a working electrode and a counter electrode is formed on an insulating support comprising polyethylene terephthalate by screen printing, and a reagent layer including an enzyme (glucose dehydrogenase with pyrrolo-quinoline quinone as coenzyme), an electron transfer agent (potassium ferricyanide), a hydrophilic polymer (carboxymethyl cellulose), aliphatic carboxylic acid (phthalic acid), and amino acid is formed on the electrodes. Thereafter, a spacer comprising polyethylene terephthalate and a cover comprising polyethylene terephthalate as well are attached, thereby manufacturing a two-electrode-system sensor for measuring a blood sugar level, in which a cavity as a capillary for leading blood is formed.

In this fifth example, eight kinds of sensors in total are manufactured as follows: sensors respectively including, as organic acids, glycine (Gly), serine (Ser), proline (Pro), threonine (Thr), lysine (Lys), sarcosine (derivative of glycine), and taurine, which are amino acids having at least one carboxyl group and one amino group in a molecule, and a conventional sensor including no amino acid.

Figure 9:
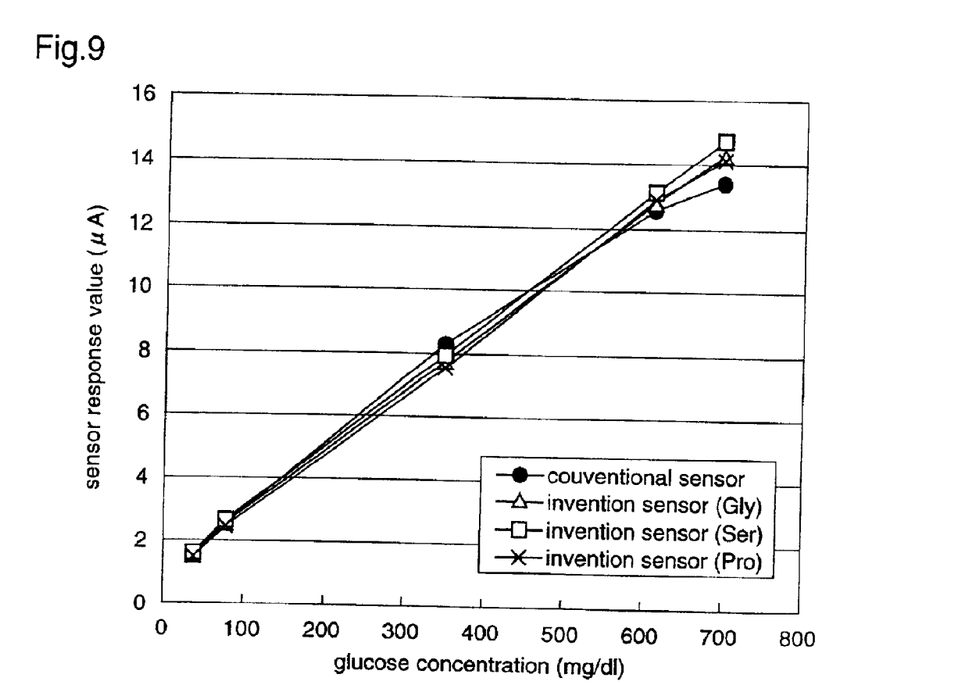
FIG. 9 is a diagram illustrating the whole blood response value when the whole blood is employed as a sample solution in a fifth embodiment.
Figure 10:
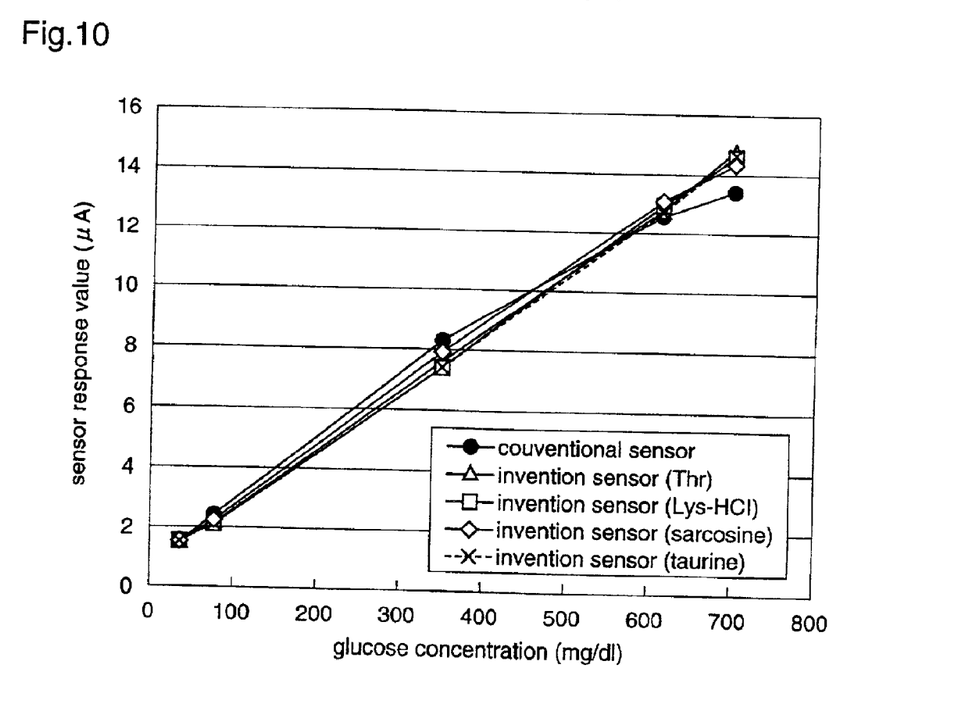
FIG. 10 is a diagram illustrating the whole blood response value when the whole blood is employed as the sample solution in the fifth embodiment.

FIGS. 9 and 10 illustrate sensor response characteristics when glucose in human whole blood is measured employing the eight sensors manufactured as described above. This fifth example employs the glucose concentrations in whole blood, 40, 80, 350, 600, and 700 mg/dl.

The measurement condition is as follows. After the cavity is filled with the sample solution (human whole blood), a reaction is promoted for twenty-five seconds. Thereafter, a voltage of 0.5V is applied between the working electrode and the counter electrode, and an electric current value obtained five seconds after the application is measured.

The number of measurement n is n=20 for each concentration, and the average thereof is plotted in the figure.

As is evident from FIGS. 9 and 10, dramatic enhancement of the response value and linearity is confirmed particularly in a range where the glucose concentration is higher than 480 mg/dL, as compared with the conventional sensor including no amino acid, although there are slight differences in the response values according to the kinds of amino acids.

Table 1 shows variations of the sensor response value at the measurement of n=20 by CV values. As is evident from table 1, considerable improvement of the CV value is recognized in the sensors of the invention which are added with amino acids. The reason is as follows. Since the amino acid added into the reagent layer prevents potassium ferricyanide from being crystallized, the reagent layer is formed smoothly and homogeneously, whereby solubility and diffusion of the reagent becomes homogeneous, resulting in a reduction of response variations.

TABLE 1

| Concentration (mg/dl) | 40 | 80 | 350 | 600 | 700 |
|---|---|---|---|---|---|
| Conventional sensor | 3.25% | 2.48% | 2.05% | 2.11% | 4.15% |
| Gly-133 mN | 2.15% | 1.75% | 1.55% | 1.28% | 1.05% |
| Ser-95 mM | 2.54% | 2.11% | 1.75% | 1.45% | 1.22% |
| Pro-87 mN | 2.38% | 1.98% | 1.69% | 1.40% | 1.18% |
| Thr-84 mN | 2.18% | 2.00% | 1.65% | 1.39% | 1.24% |
| Lys-HCl-55 mM | 2.48% | 1.89% | 1.58% | 1.41% | 1.14% |
| Sarcosine 122 mM | 2.65% | 2.08% | 1.68% | 1.35% | 1.25% |
| Taurine-80 mM | 2.18% | 1.78% | 1.43% | 1.22% | 1.10% |

While the first to fifth examples describe the biosensors for measuring the glucose concentration in blood, the sample solution and substance as targets of measurement and the type of biosensor are not restricted thereto. For example, a liquid vital specimen such as saliva, intercellular substance liquid, urine, or sweat, as well as food or drinking water, can also be employed as a target sample solution besides blood. Further, lactic acid, cholesterol, uric acid, ascorbic acid, or bilirubin, can also be also employed as a target substance besides glucose. Furthermore, As a current measurement method, there are the three-electrode system constituted by the working electrode, the counter electrode, and the detecting electrode, which is employed in the first and second examples, or the two-electrode system constituted by the working electrode and the counter electrode, which is employed in the third and fifth examples, and the same effects as described above can be obtained whichever system is employed. The three-electrode system enables more accurate measurement as compared with the two-electrode system.

While the examples are described exemplifying the enzyme sensor as a biosensor, the present invention is similarly applicable to a biosensor utilizing antibodies, microorganisms, DNA, RNA, or the like, besides enzyme, as a molecular recognition element which specifically reacts to a specific substance in a sample solution.

APPLICABILITY IN INDUSTRY

A biosensor according to the present invention includes either one or a combination of sugar alcohol, metallic salt, organic acid or organic acid salt which has at least one carboxyl group in a molecule, or organic acid or organic acid salt which has at least one carboxyl group and amino group in a molecule in its reagent, so that increase of a background electric current with time can be suppressed, a needles reaction with various contaminants existing in the blood can be suppressed, or the reagent layer can be closely and homogeneously formed, without preventing an enzyme reaction or the like, thereby providing a highly stable and efficient biosensor.

What is claimed is:

1. A biosensor for measuring the concentration of a specific substance in a sample solution, wherein
at least one type of sugar alcohol selected from the group consisting of maltitol and lactitol is included in a previously-provided reagent layer so that it is dissolved in the sample solution and specifically reacts to the specific substance in the sample solution.

2. The biosensor as defined in claim 1, wherein
the concentration of the specific substance is measured employing electrodes comprising at least a working electrode and a counter electrode provided on an insulating support.

3. The biosensor as defined in claim 2, wherein
the reagent layer is formed on the electrodes or so that the electrodes are arranged in a diffusion area where a reagent in the reagent layer is dissolved and diffused in the sample solution, and the reagent layer includes at least an enzyme and an electron transfer agent.

4. The biosensor as defined in claim 1, wherein the reagent layer further includes a hydrophilic polymer.

5. A biosensor for measuring the concentration of a specific substance in a sample solution, wherein
organic acid or organic acid salt which has at least one carboxyl group and one amino group in its molecule is included in a previously-provided reagent layer so that it is dissolved in the sample solution and specifically reacts to the specific substance in the sample solution.

6. The biosensor as defined in claim 5, wherein
the concentration of the specific substance is measured employing electrodes comprising at least a working electrode and a counter electrode provided on an insulating support.

7. The biosensor as defined in claim 6, wherein
the reagent layer is formed on the electrodes or so that the electrodes are arranged in a diffusion area where a reagent in the reagent layer is dissolved and diffused in the sample solution, and the reagent layer includes at least an enzyme and an electron transfer agent.

8. The biosensor as defined in claim 5, wherein
the organic acid is amino acid, or a substitution product or derivative of amino acid.

9. The biosensor as defined in claim 5, wherein
the amino acid is one of glycine, serine, proline, threonine, and lysine, or a combination of these acids.

10. The biosensor as defined in claim 5, wherein the reagent layer further includes a hydrophilic polymer.

11. A biosensor for measuring the concentration of a specific substance in a sample solution, wherein
a combination of at least two of at least one type of sugar alcohol selected from the group consisting of maltitol and lactitol, and organic acid or organic acid salt which has at least one carboxyl group and one amino group in its molecule, is included in a previously-provided reagent layer so that it is dissolved in the sample solution and specifically reacts to the specific substance in the sample solution.

12. The biosensor as defined in claim 11, wherein the reagent layer further includes a hydrophilic polymer.

* * * * *